(12) United States Patent
Masere

(10) Patent No.: US 9,090,526 B2
(45) Date of Patent: Jul. 28, 2015

(54) SYNERGISTIC COMBINATION FOR INHIBITING POLYMERIZATION OF VINYL MONOMERS

(75) Inventor: Jonathan Masere, Pearland, TX (US)

(73) Assignee: NALCO COMPANY, Naperville, IL (US)

( * ) Notice: Subject to any disclaimer, the term of this patent is extended or adjusted under 35 U.S.C. 154(b) by 956 days.

(21) Appl. No.: 13/158,979

(22) Filed: Jun. 13, 2011

(65) Prior Publication Data

US 2012/0316369 A1    Dec. 13, 2012

(51) Int. Cl.
*C07C 7/20* (2006.01)
*C07B 63/04* (2006.01)
*C09K 15/30* (2006.01)
*C08K 5/18* (2006.01)
*C08K 5/3475* (2006.01)
*C08K 5/13* (2006.01)
*C09K 15/08* (2006.01)
*A23L 3/3463* (2006.01)
*C08F 2/40* (2006.01)
*C07C 49/603* (2006.01)

(52) U.S. Cl.
CPC ............... *C07C 7/20* (2013.01); *C07C 49/603* (2013.01); *C08F 2/40* (2013.01)

(58) Field of Classification Search
CPC ............. C07C 7/20; C07C 15/46; C08F 2/40; C10M 2203/06; G21C 5/123; Y02E 30/40; C07B 63/04; C09K 15/30; C09K 15/08; C08K 5/005; C08K 5/18; C08K 5/3475; C08K 5/13; C10L 1/2283; A23L 3/3463; C11B 5/0035; C11B 5/0092
USPC ................... 585/2, 3, 4, 5, 403, 404
See application file for complete search history.

(56) References Cited

U.S. PATENT DOCUMENTS

| 4,003,800 | A | * | 1/1977 | Bacha et al. ............... 203/9 |
| 4,774,374 | A | | 9/1988 | Abruscato et al. |
| 5,221,764 | A | | 6/1993 | Roling |
| 5,562,863 | A | * | 10/1996 | Arhancet ............... 252/404 |
| 5,583,247 | A | | 12/1996 | Nesvadba et al. |
| 5,648,573 | A | | 7/1997 | Arhancet et al. |
| 5,670,692 | A | | 9/1997 | Nesvadba et al. |
| 5,750,765 | A | * | 5/1998 | Nesvadba et al. ......... 560/126 |
| 5,955,643 | A | | 9/1999 | Lewis |
| 6,184,276 | B1 | | 2/2001 | Ignatz-Hoover |
| 6,376,728 | B1 | * | 4/2002 | Eldin et al. ............ 585/5 |
| 6,447,649 | B1 | | 9/2002 | Arhancet |
| 6,592,722 | B2 | * | 7/2003 | Arhancet ............... 203/8 |
| 6,926,820 | B2 | | 8/2005 | Elden et al. |
| 7,045,647 | B2 | | 5/2006 | Benage |
| 7,473,795 | B2 | * | 1/2009 | Benage ............... 560/4 |
| 7,651,635 | B1 | | 1/2010 | Lewis |
| 8,247,593 | B2 | | 8/2012 | Morrison et al. |
| 2009/0114878 | A1 | * | 5/2009 | Weyler et al. ........... 252/182.29 |

* cited by examiner

*Primary Examiner* — In Suk Bullock
*Assistant Examiner* — Aaron Pierpont
(74) *Attorney, Agent, or Firm* — Benjamin Carlsen

(57) ABSTRACT

The present invention provides a method for inhibiting unwanted polymerization of reactive monomers within a liquid. The method comprises the combined usage of a quinone methide with a quinone diimide to the liquid monomer. This combination has an unexpected synergistic effect. Thus, in some ratios, the combination results in practically 100% inhibition.

20 Claims, 1 Drawing Sheet

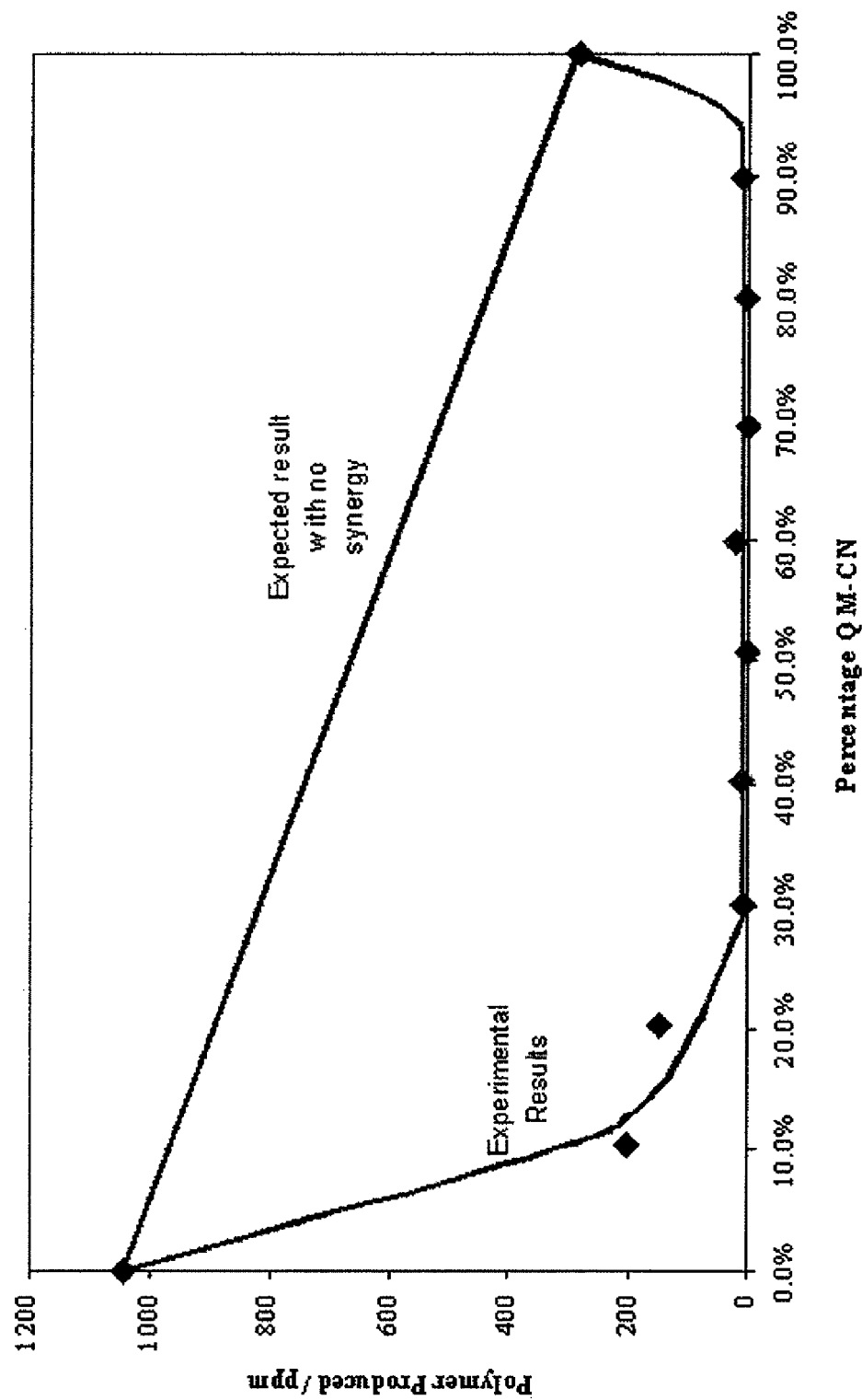

SYNERGISTIC COMBINATION FOR INHIBITING POLYMERIZATION OF VINYL MONOMERS

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to compositions of matter containing quinone methides and quinone diimides, and methods of using them to inhibit unwanted polymerization. As described in U.S. Pat. No. 7,651,635 quinone methides are used to inhibit the polymerization of vinyl aromatic monomers. Owing to their high reactivity, many of these monomers can undesirably polymerize at various stages of their manufacture, processing, handling, storage, and use. Undesirable polymerization reactions result in a loss in production efficiency because they consume valuable monomer and because they require additional purification steps to remove the undesired polymers from the process equipment and from the monomer product. During the purification process, undesired polymerization reactions are particularly problematic for vinyl aromatic monomers as they form unwanted polymer. The purification process is performed at elevated temperatures. Even in the absence of contaminants that promote polymerization, vinyl monomers, particularly aromatic vinyl monomers like styrene undergo self-initiated polymerization at high temperatures. The resultant polystyrene is linear, soluble in the styrene monomer and, therefore, can contaminate the monomer product. It is imperative to prevent unwanted polymerization.

To prevent unwanted polymerization reactions two categories of compounds have been developed, viz.; inhibitors and retarders. Inhibitors effectively prevent polymerization reactions from occurring as long as they are continuously added to the process stream. Inhibitors however are consumed rapidly unless they are continuously replenished. In cases of emergency shutdowns when, for mechanical or other operational reasons, more inhibitor cannot be added, previously added inhibitor will be rapidly consumed. Upon the complete consumption of inhibitor, the unwanted polymerization reactions will occur unabated thereafter. On the other hand, retarders slow down the rate of polymerization reactions even though they are not as effective as inhibitors. Whereas inhibitors are consumed rapidly, retarders however are not consumed as quickly but effectively keep polymer content low, therefore they are more reliable in cases of emergency shutdown conditions in which inhibitor replenishment is not possible.

To prevent unwanted polymerization reactions, only retarders such as sulfur and dinitrophenol (DNP) compounds (including 2,6-dinitrophenol, 2,4-dinitrocresol, and 2-sec-butyl-4,6-dinitrophenol (DNBP)) were initially used.

DNP and sulfur retarders however release $NO_x$ and $SO_x$ emissions, respectively. Furthermore, DNP-based retarders are highly toxic, so there is a significant need for a non-toxic replacement for them. One class of compounds that is hoped to function as safer substitute retarders for DNP is based on quinone methide architectures. Quinone methides slow the rate of polymer formation under static conditions and do not need to be frequently re-fed into the process stream. Examples of quinone methide compounds are in U.S. Pat. No. 4,003,800. As a consequence of the alkyl substituents on position 7 of the quinone methide, these compounds, however, are not stable enough for sustained use in industrial settings. Other applications of more stable quinone methides are found in U.S. Pat. No. 5,583,247, and 7,045,647.

As taught in U.S. Pat. Nos. 5,750,765, 5,670,692, 6,926,820 and 7,651,635 the stable quinone methides have proven effective and are green non-toxic alternatives for use in preventing the premature polymerization of styrene and other vinyl aromatic monomers. Therefore, there is a clear utility and novelty in effective methods of inhibiting unwanted polymerizations with compositions comprising quinone methides.

Later, two classes of inhibitors were used, these being; dialkylhydroxylamines (including hydroxypropylhydroxylamine (HPHA)) and stable nitroxide free radicals. Other inhibitors have been used since then. Examples are N,N'-dialkylphenylenediamines, N,N'-diarylphenylenediamines N-aryl-N'-alkylphenylenediamines. Quinone diimide compounds are also another class of inhibitors. The use of quinone diimides is taught in U.S. Pat. No. 4,774,374, U.S. Pat. No. 5,562,863, U.S. Pat. No. 6,184,276, U.S. Pat. No. 6,447,649 and U.S. Pat. No. 6,592,722.

To ensure safety in the event of a plant malfunction, inhibitors are typically not to be used alone but are often combined with retarders.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists. Any and all patents, patent applications, and other references cited by this application are hereby incorporated by reference in their entirety.

BRIEF SUMMARY OF THE INVENTION

At least one embodiment of the invention is directed towards a method for inhibiting the polymerization of vinyl monomers in a liquid comprising adding to said monomers a composition comprising Compound A and Compound B wherein:

Compound A is a quinone methide compound with the formula:

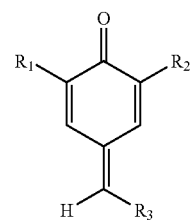

wherein $R_1$ and $R_2$ are independently H, $C_4$ to $C_{18}$ alkyl; $C_5$ to $C_{12}$ cycloalkyl; $C_7$ to $C_{15}$ phenylalkyl, and any combination thereof. Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred, and, $R_3$ is preferably aryl, or aryl substituted with $C_1$ to $C_6$ alkyl, alkoxy, nitro, amino and carboxy, and $R_3$ is also preferably nitrile, methoxy, 4-hydroxy-3,5-di-tert-butylphenyl, an acetylenic group, or phenyl-substituted acetyleno preferably substituted with $C_1$ to $C_6$ alkyl, alkoxy, nitro, amino and carboxy;

At least one embodiment of the invention is directed towards a composition comprising Compound A and Compound B wherein:

Compound B is a quinone diimide compound of the formula:

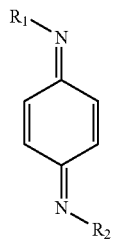

in which substituents $R_1$ and $R_2$ are the same or different and are alkyl, aryl, alkaryl, aralkyl group, and any combination thereof, wherein the weight ratio of Compound A to Compound B is about 9:1 to about 1:9 and Compound A may be a stable quinone methide. Suitable examples of quinone methides are 7-cyano quinone methide (2-(3,5-di-tert-butyl-4-oxocyclohexa-2,5-dienylidene)acetonitrile, a 7-substituted-quinone methide also called 2,6-di-tert-butyl-7-cyano quinone methide), 4-Benzylidene-2,6-di-tert-butyl-cyclohexa-2,5-dienone also called 7-phenyl quinone methide, 2,6-di-tert-butyl-4-(methoxymethylene)cyclohexa-2,5-dienone also called 7-methoxy quinone methide, and 2,6-di-tert-butyl-4-(3,5-di-tert-butyl-4-hydroxybenzylidene)cyclohexa-2,5-dienone also called 7-(4-hydroxy-3,5-di-tert-butylphenyl) quinone methide.

Compound B may be a quinone diimide. The quinone diimide may be benzoquinonediimide compound N,N'-(cyclohexa-2,5-diene-1,4-diylidene)dibutan-1-amine, benzoquinonediimide compound (E)-N-((E)-4-(4-methylpentan-2-ylimino)cyclohexa-2,5-dienylidene)aniline, and any combination thereof. The monomer may be a vinylic monomer. The amount of said composition added to the monomer may vary from 1 to 10,000 parts per million of said monomer. The weight proportion of Compound A to Compound B may be between about 9:1 and about 1:9 to about 1:1 and/or from 4:6 to 6:4. The polymerization may be substantially inhibited. The polymerization may be inhibited within an anaerobic environment. The inhibition may be more effective than the linear combination of the effectiveness of an inhibitor consisting essentially of Compound B plus the effectiveness of an inhibitor consisting essentially of Compound A.

Compound A may be a quinone methide compound with the formula;

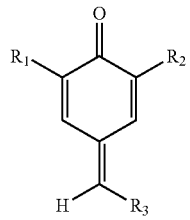

wherein $R_1$ and $R_2$ are independently H, $C_4$ to $C_{18}$ alkyl; $C_5$ to $C_{12}$ cycloalkyl; or $C_7$ to $C_{15}$ phenylalkyl. Preferably, $R_1$ and $R_2$ are text-butyl, tert-amyl, tert-octyl, cyclohexyl, α-methylbenzyl or α,α-dimethylbenzyl; with tert-butyl, tert-amyl or tert-octyl most preferred, and, $R_3$ is also preferably nitrile, aryl, methoxy, 4-hydroxy-3,5-di-tert-butylphenyl, an acetylenic group, or phenyl-substituted acetyleno preferably substituted with $C_1$ to $C_6$ alkyl, alkoxy, nitro, amino and carboxy, and (B) a quinone diimide compound of the formula

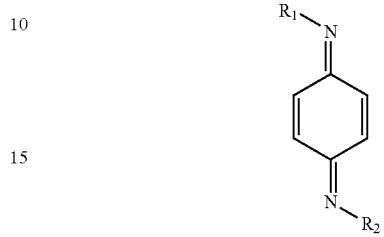

in which substituents $R_1$ and $R_2$ are the same or different and are alkyl, aryl, alkaryl, or aralkyl groups wherein the weight ratio of Compound A to Compound B is about 9:1 to about 1:9.

The quinone methide compounds may be (2-(3,5-di-tert-butyl-4-oxocyclohexa-2,5-dienylidene)acetonitrile (also called 7-cyano quinone methide), 2,6-di-tert-butyl-4-(methoxymethylene)cyclohexa-2,5-dienone (also called 7-methoxy quinone methide), 2,6-di-tert-butyl-4-(3,5-di-tert-butyl-4-hydroxybenzylidene)cyclohexa-2,5-dienone (also called 7-(4-hydroxy-3,5-di-tert-butylphenyl)quinone methide) and 4-benzylidene-2,6-di-tert-butyl-cyclohexa-2,5-dienone (also called 7-phenyl quinone methide).

The quinone diimide compound may be N,N-(cyclohexa-2,5-diene-1,4-diylidene)dibutan-1-amine, (E)-N-((E)-4-(4-methylpentan-2-ylimino)cyclohexa-2,5-dienylidene)aniline. The weight ratio of Compound A and Compound B may be between about 9:1 to about 1:9 or about 4:6 to 6:4. There may be is synergism between Compound A and Compound B as an inhibitor of vinyl monomer polymerization.

BRIEF DESCRIPTION OF THE DRAWINGS

FIG. 1 illustrates a graph demonstrating the synergistic inhibition effect of the invention.

DETAILED DESCRIPTION OF THE INVENTION

For purposes of this application the definition of these terms is as follows:

"Alkoxy" means an alkyl group, as defined herein, attached to the parent molecular moiety through an oxygen atom. Representative alkoxy groups include methoxy, ethoxy, propoxy, butoxy, and the like.

"Alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, n-octyl, and the like.

"Combination" means the combined usage of two or more compounds to yield a composition that inhibits undesirable polymerization.

"Effective Inhibiting Amount" means that amount of inhibitor composition which is effective at inhibiting vinyl aromatic monomer polymerization.

"Induction time" means the period of time in which in an ideal closed system a composition of matter completely prevents the formation of a particular polymer during a given reaction.

"Inhibitor" means a composition of matter that inhibits the formation of the particular polymer during an induction time but after the induction time has lapsed, the particular polymer's formation occurs at substantially the same rate that it would form at in the absence of the composition of matter.

"Retarder" means a composition of matter, which does not have an induction time, but instead once added to the given reaction the composition of matter reduces the rate at which the formation of the particular polymer occurs relative to the rate at which it would have formed in the absence of the composition of matter.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

In at least one embodiment, invention is directed to compositions which comprise a quinone methide derivative and a quinone diimide. These compositions inhibit the unwanted polymerization of vinyl monomers.

The quinone methide derivatives of the present invention commonly have the chemical structure:

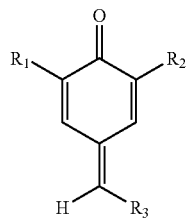

wherein $R_1$ and $R_2$ are independently H, $C_4$ to $C_{18}$ alkyl; $C_5$ to $C_{12}$ cycloalkyl; or $C_7$ to $C_{15}$ phenylalkyl. Preferably, $R_1$ and $R_2$ are tert-butyl, tert-amyl, tert-octyl, cyclohexyl, α-methylbenzyl or α,α-dimethylbenzyl; with tert-butyl, tert-amyl or tert-octyl most preferred.

$R_3$ is preferably aryl, or aryl substituted with $C_1$ to $C_6$ alkyl, alkoxy, nitro, amino, carboxy, or nitrile, or acetylenic group, or acetyleno substituted with a phenyl or substituted phenyl group, or acetyleno substituted with $C_1$ to $C_6$ alkyl, alkoxy, nitro, amino, carboxy group.

Preferably, the quinone methide derivative is 2-(3,5-di-tert-butyl-4-oxocyclohexa-2,5-dienylidene)acetonitrile (a 7-substituted-quinone methide also called 2,6-di-tert-butyl-7-cyano quinone methide or 7-cyano quinone methide), 4-Benzylidene-2,6-di-tert-butyl-cyclohexa-2,5-dienone also called 7-phenyl quinone methide, 2,6-di-tert-butyl-4-(methoxymethylene)cyclohexa-2,5-dienone also called 7-methoxy quinone methide, and 2,6-di-tert-butyl-4-(3,5-di-tert-butyl-4-hydroxybenzylidene)cyclohexa-2,5-dienone also called 7-(4-hydroxy-3,5-di-tert-butylphenyl)quinone methide.

The quinone diimide compound of the present invention comprises a benzoquinonediimide compound which typically has the general formula:

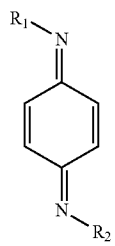

in which substituents $R_1$ and $R_2$ are the same or different and are alkyl, aryl, alkaryl, or aralkyl groups. The preferable benzoquinonediimide compound is selected from the group consisting of N,N'-dialkyl-p-benzoquinonediimides and N-phenyl-N'-alkyl-p-benzoquinonediimides. The benzoquinonediimide compound may also be selected from the group consisting of N,N'-di-sec-butyl-p-benzoquinonediimide, N-phenyl-N'-methyl-p-benzoquinonediimide, N-phenyl-N'-ethyl-p-benzoquinonediimide, N-phenyl-N'-propyl-p-benzoquinonediimide, N-phenyl-N'-n-butyl-p-benzoquinonediimide, N-phenyl-N'-iso-butyl-p-benzoquinonediimide, N-phenyl-N'-sec-butyl-p-benzoquinonediimide, N-phenyl-N'-tert-butyl-p-benzoquinonediimide, N-phenyl-N'-n-pentyl-p-benzoquinonediimide, N-phenyl-N'-(1-methylhexyl)-p-benzoquinonediimide, N-phenyl-N'-(1,3-dimethylhexyl)-p-benzoquinonediimide, N,N'-bis(1,4-dimethylpentyl)-p-benzoquinonediimide, N-phenyl-N'-(1,4-dimethylpentyl)-p-benzoquinonediimide and N-phenyl-N'-(1,4-dimethylbutyl)-p-benzoquinonediimide.

Preferred benzoquinonediimide compounds comprise N,N-(cyclohexa-2,5-diene-1,4-diylidene)dibutan-1-amine and (E)-N-((E)-4-(4-methylpentan-2-ylimino)cyclohexa-2,5-dienylidene)aniline.

In at least one embodiment unwanted polymerization within a target liquid environment is inhibited by the addition of a quinone methide bearing composition into the monomer solution. The composition comprises at least one form of quinone methide and at least one form of phenylenediamine oxidized to quinone diimide. Prior to making the composition, the phenylenediamines are initially oxidized into quinone diimides. Alternatively, commercially available quinone diimide compounds can be used. The quinone diimide is then combined with a quinone methide and in this form it effectively inhibits polymerization.

In at least one embodiment, the combination occurs in a manner similar to the methods and procedures described in U.S. Pat. No. 5,955,643 whereby a combination of a stable nitroxide radical and non-toxic phenylenediamine is used to inhibit undesirable polymerization of styrene under anaerobic conditions. A significant difference is the fact that in this current invention, in the quinone diimide and quinone methide combination, the phenylenediamine is already oxidized to a quinone diimide and the combination relies upon a quinone diimide in the place of a nitroxide. Instead of oxidizing the phenylenediamine to quinone diimide in situ, the phenylenediamine is oxidized prior to the injection into the process stream. In at least one embodiment the combination consists of a quinone methide and a quinone diimide. The composition may comprise other materials as well as the combination.

In the past, different inhibitor combinations have been attempted. As an example HTEMPO has been combined with other inhibitors to address technical and economic deficiencies with using HTEMPO alone. These combinations, however, did not result in the combination having an overall inhibiting capability greater than the linear sum of their constituents. Moreover it is often the case that inhibitor combinations produce worse rather than better results than their constituents do alone. Thus it is quite unexpected that this quinone diimide-quinone methide combination displays such a strong synergistic effect displaying stronger antipolymerant activity than would be expected from the linear combination of the effectiveness of quinone diimide with the effectiveness of quinone methide.

While quinone diimides have previously been used to stabilize unwanted polymerizations, the effectiveness of those previous uses convincingly demonstrates that the effectiveness of this combination is quite unexpected. In U.S. Pat. No. 4,774,374 by co-injecting oxygen, a phenylenediamine is oxidized in situ to a quinone diimide, which is used to stabilize a vinyl aromatic monomer from polymerizing. The phenylenediamine, however, is ineffective in anaerobic conditions while the quinone diimide-quinone methide combination is effective in anaerobic conditions or in other oxygen deficient situations. U.S. Pat. No. 5,221,764 describes the combined use of a cerium compound and a phenylenediamine compound that generates a quinone diimide in situ which effectively inhibits acrylic acid polymerization at high temperatures.

In at least one embodiment, the quinone diimide need not be generated in situ. The use of quinone diimide is taught in U.S. Pat. Nos. 6,184,276 and 6,376,728. In U.S. Pat. No. 5,562,863, a quinone diimide is used in combination with 2,6-di-tert-butyl-4-methylphenol. U.S. Pat. No. 5,648,573 teaches the combined usage of a quinone diimide and a hydroxylamine. Furthermore, U.S. Pat. Nos. 6,447,649 and 6,592,722 teach the combined usage of a quinone diimide and a stable nitroxide radical as inhibitors of undesirable polymerization of vinyl monomers.

In at least one embodiment, the compositions of the present invention efficaciously inhibit undesirable polymerization of vinyl aromatic monomers under processing conditions. These processing conditions include but are not restricted to preparation, purification, distillation and vacuum distillation processes. As a typical example, styrene is processed at temperatures between 95° and 125° C. The compositions of the present invention are effective at inhibiting the polymerization of styrene over this temperature range. The compositions are particularly efficient at inhibiting the polymerization of styrene monomer.

In at least one embodiment, the total amount of quinone methide derivative and quinone diimide compound used in the methods of the present invention is that amount which is sufficient to inhibit polymerization of vinyl aromatic monomers. The conditions, such as presence of contaminants in the system and the process temperature, of the system under which the vinyl aromatic monomer is being processed will determine the amount of the composition used. Accordingly, larger amounts of the inhibiting composition are required at higher processing temperatures and monomer with higher concentrations of contaminants.

The preferred amount of quinone methide derivative and quinone diimide composition ranges from about 1 part to about 10,000 parts per 1 million parts of monomer. Most preferably, this amount will range from about 1 part total to about 1000 parts per million parts monomer.

By combining a quinone methide compound and a quinone diimide compound, it is possible for the resultant composition to produce a more effective vinyl aromatic monomer polymerization inhibiting treatment than is obtained by the use of either compound by itself when measured at comparable treatment levels. The subsequent synergy or enhanced activity between components allows for the concentration of each of the components to be lowered such that the total quantity of the polymerization inhibitor required is concomitantly lowered while achieving a commensurate level of polymerization inhibition.

As such, the mole percent of quinone methide compound to quinone diimide compound in the composition will generally vary from about 1:99 to about 99:1, with a mole percent ratio of about from about 30:70 to about 90:10 preferred. Most preferably, the mole percent ratio is about 50:50.

Without being limited in the scope of the invention and in particular in the construal of the claims, it is believed that the quinone methide provides flexibility in use and the quinone diimide provides a high level of effectiveness which together result in significant synergy.

EXAMPLES

The foregoing may be better understood by reference to the following examples, which are presented for purposes of illustration and are not intended to limit the scope of the invention.

Example 1

The uninhibited solution was prepared and tested for unwanted polymer as follows: A solution containing 5.25 g of styrene, 5 ml of n-octane and 6 ml of xylene was prepared in a glass container (Petrotest, Ref. 13-0533). Toluene was then added to the solution up to a total mass of 20.882 g. A glass lid (Petrotest, Ref. 13-0514) was fitted to the container, it was placed inside a closed reaction vessel known as a bomb (Petrotest, Ref. 13-1141) and the lid of the bomb was closed. An 8 bar, high-purity nitrogen supply (containing <10 ppb oxygen) was used to purge the bomb six times. This involved the use of a 3-way valve (Swagelok, Ref. SS-43GXF4) that allowed the bomb to be filled and partially emptied, along with allowing the line to be purged between each fill. The bomb was finally pressurized to 100 psi with nitrogen. The bomb was set to TEST for 30 minutes, which determined if there were any leaks in the system. If the reactor passed this leak test it was placed in a heat bath at 130° C. for 2 hours. Upon removal from the heat bath the bomb was allowed to cool to room temperature before being depressurized and having the glass container removed. The amount of polymer produced was measured. The average concentration of unwanted polymer in the untreated (blank) test was 19778 ppm with a standard deviation of 4032 ppm.

Example 2

The treated solutions were prepared and tested for unwanted polymer according to the procedure in Example 1. As the inhibitors all have different molecular weights, molar concentration was used for this investigation instead of milligrams of inhibitor per 1 kilogram of solution (ppm).

Initially experiments were carried out with a total inhibitor concentration of 0.145 mM, the equivalent to 25 ppm of HTEMPO. Before any combinations were tested, the quinone methide and quinone diimide were each separately tested at a concentration of 0.145 mM. Thereafter, the performance of different combinations was investigated. The two components were in molar concentrations but the total concentration was kept constant at 0.145 mM. The mole percent of quinone methide relative to the mole percent of quinone diimide ranged from 0:100 to 100:0. Preferably, the mole percent of quinone methide relative to the mole percent of quinone diimide ranged from 10:90 to 90:10; more preferably from 30:90 to 90:10; more preferably about 50:50.

The results are found in Table 1 herein below, and also in FIG. 1.

| Quinone Methide (mole %) | Quinone Diimide (mole %) | Polymer (ppm) |
|---|---|---|
| 0.0 | 0.0 | 19778 |
| 100 | 0 | 283 |
| 90 | 10 | 13.1 |
| 80 | 20 | 4.5 |
| 70 | 30 | 0.5 |
| 60 | 40 | 21.3 |
| 50 | 50 | 0.0 |
| 40 | 60 | 11.4 |
| 30 | 70 | 7.9 |
| 20 | 80 | 147 |
| 10 | 90 | 203 |
| 0 | 100 | 1045 |

As illustrated in FIG. 1, a series of samples of inhibitor combinations were prepared. The combinations comprised various proportions of quinone methides (in particular 7-cyano quinone methide (QM-CN)) and oxidized (E)-N-RE)-4-(4-methylpentan-2-ylimino)cyclohexa-2,5-dienylidene) aniline. The effectiveness of the various samples at inhibiting polymerization of vinyl monomers was compared to a linear representation of the "gap" between the effectiveness QM-CN and (E)-N-((E)-4-(4-methylpentan-2-ylimino)cyclohexa-2,5-dienylidene)aniline by themselves. The data shows that when the proportion of quinone methide is between 30% and 90% of the combination, the inhibitor is nearly 100% effective and even when outside of this range, the combination is still more effective than either quinone diimide or quinone methide alone. Thus the unexpected synergistic effect seems to be present by all combinations of the two.

While this invention may be embodied in many different forms, there are shown and described in detail herein specific preferred embodiments of the invention. The present disclosure is an exemplification of the background and principles of the invention and is not intended to limit the invention to the particular embodiments illustrated. All patents, patent applications, scientific papers, and any other referenced materials mentioned anywhere herein, are incorporated by reference in their entirety. Furthermore, the invention encompasses any possible combination of some or all of the various embodiments explicitly described herein and incorporated herein as well as combinations which exclude one, some, or all but one of the various embodiments explicitly described and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of inhibiting polymerization of vinyl monomers in a liquid, comprising adding to said liquid a composition comprising Compound A and Compound B, wherein:

Compound A is a quinone methide compound with the formula:

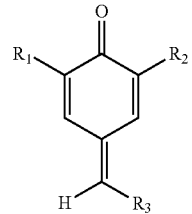

wherein $R_1$ and $R_2$ may be the same or different and each of $R_1$ and $R_2$ is selected from the group consisting of H, $C_4$ to $C_{18}$ alkyl, $C_5$ to $C_{12}$ cycloalkyl, $C_7$ to $C_{15}$ phenylalkyl, and any combination thereof, and $R_3$ is an aryl, an aryl substituted with $C_1$ to $C_6$ alkyl, an alkoxy, a nitro, an amino, a carboxy, a nitrile, a methoxy, 4-hydroxy-3,5-di-tert-butylphenyl, an acetylenic group, a phenyl-substituted acetyleno, a phenyl-substituted acetyleno substituted with $C_1$ to $C_6$ alkyl, alkoxy, nitro, amino, carboxy, and any combination thereof;

Compound B is a quinone diimide compound of the formula:

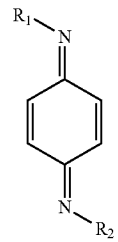

wherein $R_1$ and $R_2$ may be the same or different and each of R1 and R2 is selected from the group consisting of an alkyl, an aryl, an alkaryl, and an aralkyl; wherein the weight ratio of Compound A to Compound B is from about 9:1 to about 1:9, and the polymerization is inhibited within an anaerobic environment.

2. The method of claim 1, wherein Compound A is a stable quinone methide selected from the group consisting of: 2-(3,5-di-tert-butyl-4-oxocyclohexa-2,5-dienylidene)acetonitrile; 2,6-di-tert-butyl-7-cyano quinone methide; 4 benzylidene-2,6-di-tert-butyl-cyclohexa-2,5-dienone; 2,6-di-tert-butyl-4-(methoxymethylene)cyclohexa-2,5-dienone; 2,6-di-tert-butyl-4-(3,5-di-tert-butyl-4-hydroxybenzylidene)cyclohexa-2,5-dienone; and any combination thereof.

3. The method of claim 1, wherein Compound B is benzoquinonediimide compound N,N'-(cyclohexa-2,5-diene-1,4-diylidene)dibutan-1-amine.

4. The method of claim 1, wherein Compound B is benzoquinonediimide compound (E)-N-((E)-4-(4-methylpentan-2-ylimino)cyclohexa-2,5-dienylidene)aniline.

5. The method of claim 1, wherein said composition is added to the liquid in an amount of from about 1 to about 10,000 parts per million of said monomer.

6. The method of claim 1, wherein the weight proportion of Compound A to Compound B is about 1:1.

7. The method of claim 1, wherein the weight proportion of Compound A to Compound B ranges from about 6:4 to about 4:6.

8. The method of claim 1, wherein the polymerization is substantially inhibited.

9. The method of claim 1, wherein the inhibition is more effective than the linear combination of the effectiveness of an inhibitor consisting essentially of Compound B with the effectiveness of an inhibitor consisting essentially of Compound A.

10. The method of claim 1, wherein said composition is added to the liquid in an amount of from about 1 to about 1000 parts per million of said monomers.

11. The method of claim 1, wherein the weight ratio of Compound A to Compound B is from about 9:1 to about 3:7.

12. The method of claim 1, wherein, when $R_1$ is not H, $R_1$ is selected from the group consisting of tert-butyl, tert-amyl, tert-octyl, cyclohexyl, $\alpha$-methylbenzyl, $\alpha,\alpha$-dimethylbenzyl, and any combination thereof.

13. The method of claim 1, wherein, when $R_2$ is not H, $R_2$ is selected from the group consisting of tert-butyl, tert-amyl, tert-octyl, cyclohexyl, $\alpha$-methylbenzyl, $\alpha,\alpha$-dimethylbenzyl, and any combination thereof.

14. A method of inhibiting polymerization of vinyl monomers in a liquid comprising adding to said liquid a composition comprising Compound A and Compound B, wherein:
Compound A is a quinone methide compound with the formula:

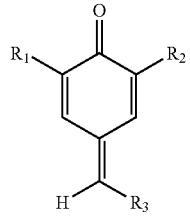

wherein $R_1$ and $R_2$ may be the same or different and each of $R_1$ and $R_2$ is selected from the group consisting of H, $C_4$ to $C_{18}$ alkyl, $C_5$ to $C_{12}$ cycloalkyl, $C_7$ to $C_{15}$ phenylalkyl, and any combination thereof, and, $R_3$ is aryl, or aryl substituted with $C_1$ to $C_6$ alkyl, alkoxy, nitro, amino and carboxy, nitrile, methoxy, 4-hydroxy-3,5-di-tert-butylphenyl, an acetylenic group, or phenyl-substituted acetyleno, phenyl-substituted acetyleno substituted with $C_1$ to $C_6$ alkyl, alkoxy, nitro, amino, carboxy, and any combination thereof;
Compound B is a quinone diimide compound selected from the group consisting of: a N,N'-dialkyl-p-benzoquinonediimide, a N-phenyl-N'-alkyl-p-benzoquinonediimide, and combinations thereof; wherein the weight ratio of Compound A to Compound B is from about 9:1 to about 1:9, and the polymerization is inhibited within an anaerobic environment.

15. The method of claim 14, wherein said composition is added to the liquid in an amount of from about 1 to about 10,000 parts per million of said monomer.

16. The method of claim 14, wherein said composition is added to the liquid in an amount of from about 1 to about 1000 parts per million of said monomer.

17. The method of claim 14, wherein the weight proportion of Compound A to Compound B ranges from about 9:1 to about 3:7.

18. The method of claim 14, wherein wherein the weight proportion of Compound A to Compound B ranges from about 6:4 to about 4:6.

19. The method of claim 14, wherein the weight proportion of Compound A to Compound B is about 1:1.

20. A method of inhibiting polymerization of vinyl monomers in a liquid comprising adding to said liquid a composition comprising Compound A and Compound B, wherein:
Compound A is a quinone methide compound with the formula:

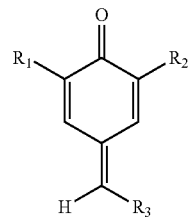

wherein $R_1$ and $R_2$ may be the same or different and each of $R_1$ and $R_2$ is selected from the group consisting of H, $C_4$ to $C_{18}$ alkyl, $C_5$ to $C_{12}$ cycloalkyl, $C_7$ to $C_{15}$ phenylalkyl, and any combination thereof, and $R_3$ is aryl, or aryl substituted with $C_1$ to $C_6$ alkyl, alkoxy, nitro, amino and carboxy, nitrile, methoxy, 4-hydroxy-3,5-di-tert-butylphenyl, an acetylenic group, or phenyl-substituted acetyleno, phenyl-substituted acetyleno substituted with $C_1$ to $C_6$ alkyl, alkoxy, nitro, amino, carboxy, and any combination thereof;
Compound B is a quinone diimide compound selected from the group consisting of: N,N'-di-sec-butyl-p-benzoquinonediimide, N-phenyl-N'-methyl-p-benzoquinonediimide, N-phenyl-N'-ethyl-p-benzoquinonediimide, N-phenyl-N'-propyl-p-benzoquinonediimide, N-phenyl-N'-n-butyl-p-benzoquinonediimide, N-phenyl-N'-iso-butyl-p-benzoquinonediimide, N-phenyl-N'-sec-butyl-p-benzoquinonediimide, N-phenyl-N'-tert-butyl-p-benzoquinonediimide, N-phenyl-N'-n-pentyl-p-benzoquinonediimide, N-phenyl-N'-(1-methylhexyl)-p-benzoquinonediimide, N-phenyl-N'-(1,3-dimethylhexyl)-p-benzoquinonediimide, N,N'-bis(1,4-dimethylpentyl)-p-benzoquinonediimide, N-phenyl-N'-(1,4-dimethylpentyl)-p-benzoquinonediimide and N-phenyl-N'-(1,4-dimethylbutyl)-p-benzoquinonediimide, and combinations thereof; wherein the weight ratio of Compound A to Compound B is from about 9:1 to about 1:9, and the polymerization is inhibited within an anaerobic environment.

* * * * *